United States Patent
Ishikawa et al.

[11] Patent Number: 5,878,107
[45] Date of Patent: Mar. 2, 1999

[54] X-RAY RADIOGRAPH APPARATUS

[75] Inventors: Ken Ishikawa, Matsudo; Fumitaka Takahashi, Toride; Hiroshi Tazaki, Kashiwa; Takashi Ishiguro, Tokyo, all of Japan

[73] Assignee: Hitachi Medical Corporation, Chiyodo-ku, Japan

[21] Appl. No.: 812,405

[22] Filed: Mar. 5, 1997

[30] Foreign Application Priority Data

Mar. 8, 1996 [JP] Japan ..................................... 8-051297
Oct. 24, 1996 [JP] Japan ..................................... 8-282304

[51] Int. Cl.$^6$ ..................................................... A61B 6/00
[52] U.S. Cl. ........................ 378/98.2; 378/98.8; 378/116
[58] Field of Search ................................ 378/98.2, 98.3, 378/98.7, 98.8, 98.9, 114, 115, 116

[56] References Cited

U.S. PATENT DOCUMENTS

| | | | |
|---|---|---|---|
| 4,442,538 | 4/1984 | Haendle | 378/98.3 X |
| 4,658,413 | 4/1987 | Nishioka et al. | 378/114 X |
| 5,117,446 | 5/1992 | Haaker et al. | 378/98.3 |
| 5,177,777 | 1/1993 | Niino | 378/98.3 |
| 5,353,325 | 10/1994 | Ueda et al. | 378/98.2 |
| 5,394,455 | 2/1995 | Roeck et al. | 378/98.3 |

FOREIGN PATENT DOCUMENTS

49-35277  10/1975  Japan .
60-276856  6/1987  Japan .

*Primary Examiner*—David P. Porta
*Attorney, Agent, or Firm*—Thelen, Reid & Priest LLP

[57] ABSTRACT

An X-ray radiograph apparatus comprising an X-ray source which irradiates a subject body with X rays of a low level radiation dose during the fluoroscopic operation and irradiates the same with X rays of a high level radiation dose during the radiographic operation; an X-ray image intensifier for converting an X-ray image, which has irradiated by the X-ray source and has penetrated through the subject body, into an optical image; a distributor for distributing an output optical image from the X-ray intensifier to a plurality of optical paths; a fluoroscopic imaging element arranged on one of plural output optical paths of the distributor; a radiographic imaging element arranged on an output optical path of the distributor other than the output optical path on which the fluoroscopic imaging element is arranged, the radiographic imaging element having a higher resolution than the fluoroscopic imaging element and having a lower imaging speed than the fluoroscopic imaging element; and an image display for displaying a fluoroscopic image or a radiographic image formed based on output signals from the fluoroscopic imaging element or the radiographic imaging element, respectively. With this, it becomes possible to collect, at the same time, the high resolution static image (radiographic image) by the radiographic imaging element and the moving image (fluoroscopic image) by the fluoroscopic imaging element. It is also possible to improve the S/N ratio of the radiographic image. Furthermore, should the radiographic image element include a defect pixel, the influence thereby would be lowered to minimum or to zero.

22 Claims, 5 Drawing Sheets

X-RAY RADIOGRAPH APPARATUS

FIELD OF THE INVENTION

The present invention generally relates to an X-ray radiograph apparatus which irradiates a subject body with X rays to obtain a fluoroscopic or radiographic image of a diagnostic part in the subject body using some devices such as an X-ray image intensifier and a television camera, and displays the image on the screen of a display, and more particularly relates an X-ray radiograph apparatus in which an imaging element or device is made use of, thereby enabling a static image and a moving image as well to be collected with high resolution.

DESCRIPTION OF THE RELATED ART

In the field of diagnosis using the X-ray radiography, it is expected that digitization of the radiograph would well contribute to the instantaneous display of the radiograph and diagnosis thereby, improvement in operability of diagnostic radiograph equipments, each access to electronic networks and so forth. In compliance with such expectation, for instance, there has been realized a high resolution digital radiograph apparatus (referred to as DR apparatus hereinafter) of the class with 2000 scanning lines, which uses an image tube, as a digital radiograph apparatus which uses an X-ray image pickup system consisting of an X-ray image intensifier and a television camera and produces a high resolution fluoroscopic X-ray image by taking a digitized image in a frame memory. In case of the high resolution DR apparatus, however, pixels of at least one million are required to obtain an image equivalent to a fluoroscoped image by the prior art X-ray image intensifier while pixels of at least four millions are needed for obtaining an image equivalent to an image by the X-ray radiography.

Recently, on one hand, a CCD imaging element using CCD (charge-coupled device) has been indicating a rapid progress in its technology. Comparing with the image tube, CCD is compact, of light weight, and low in price, and it has become a device easy to adjust. With the background like this, it has been often recognized that prior art image tubes are replaced by CCDs. Several methods are available as a way of producing a high resolution image by CCD, for instance, a method of using a single CCD of very high resolution including pixels of several millions, or a method of using a plurality of ordinary resolution CCDs, each including pixels of 800 thousands or so per unit. Technology for obtaining a high resolution image by making use of CCD imaging elements is described in the specification of the Japanese Patent Application No. 49-35277 and also described in the specification of the Japanese Patent Application No. 60-276856.

However, in case of realizing a high resolution DR apparatus of the class with 2000 scanning lines by using a CCD imaging element, there arise the following problems. First, in case of using a very high resolution CCD including pixels of several millions, the scanning mode is fixed different from the case of using the image tube, so that it is difficult to collect a high resolution static image and a moving image at the same moment. In the second, when the number of pixels is increased up to the order of several millions, it becomes difficult to obtain a CCD imaging element without any defect pixel. In case of using a plurality of ordinary resolution DDC imaging element, however, precise adjustment is required with respect to location and direction for setting it up, and its gain, regardless of the way of picking up the image, namely, by way of dividing the entire image into several parts or by way of shifting pixels. At this time, if the adjustment is insufficiently carried out, it might happen that a certain artifact is caused in the joint area of the image. Furthermore, the maximum electric charge accumulation in the CCD imaging element is smaller comparing with the image tube, so that the S/N ratio with regard to the well lighted part of the image becomes worse.

SUMMARY OF THE INVENTION

Accordingly, an object of the invention is to provide an X-ray radiograph apparatus using imaging elements wherein a high resolution static image (radiographic image) and a moving image (fluoroscopic image) can be obtained at the same time.

Another object of the invention is to improve the S/N ratio of the radiographic image.

Still another object of the invention is to enable the influence of a defect pixel to be lowered ro zero, should it be included in the radiographic imaging element.

Still another object of the invention is to constitute the image pickup device in such a compact form that lessens the limitation on its movement range and at the same time, an operator's works is not disturbed by the movement of the image pickup device.

In order to achieve the objects as mentioned above, the invention provides an X-ray radiograph apparatus comprising an X-ray source which irradiates a subject body with X rays of a low level radiation dose during the fluoroscopic operation and irradiates the same with X rays of a high level radiation dose during the radiographic operation; an X-ray image intensifier for converting an X-ray image, which is formed of X rays emitted from the X-ray source and penetrated through the subject body, into an optical image; a distributor for distributing an output optical image from the X-ray image intensifier to a plurality of optical paths; a fluoroscopic imaging element arranged on one of plural output optical paths of the distributor; a radiographic imaging element arranged on an output optical path of the distributor other than the output optical path on which the fluoroscopic imaging element is arranged, the radiographic imaging element having a higher resolution than the fluoroscopic imaging element and having a lower imaging speed than the fluoroscopic imaging element; and an image display for displaying a fluoroscopic image or a radiographic image formed based on output signals from the fluoroscopic imaging element or the radiographic imaging element, respectively.

In the above X-ray radiograph apparatus, an output optical image from the distributor is input to the fluoroscopic imaging element and radiographic imaging element at the same time.

The above-mentioned X-ray radiograph apparatus further comprises an image processor which performs an image processing for displaying, on the screen of the image display, the X-ray fluoroscopic image signals obtained by the fluoroscopic imaging element and/or the X-ray radiographic image signals obtained by the radiographic imaging element, and which produces the image data for display use by composing the X-ray fluoroscopic image signals and the X-ray radiographic image signals which are simultaneously output from the distributor.

In the above X-ray radiograph apparatus, a shutter is provided between the distributor and the radiographic imaging element.

In the above X-ray radiograph apparatus, the above shutter is opened in response to a start signal of X-ray irradiation for radiographing and closed in response to a signal indicative of the end of radiographing.

The above-mentioned X-ray radiograph apparatus further comprises an image processor which performs an image processing for displaying, on the screen of the image display, the X-ray fluoroscopic image signals obtained by the fluoroscopic imaging element or the X-ray radiographic image signals obtained by the radiographic imaging element.

In the above X-ray radiograph apparatus, the distributor has a half-mirror which divides an incident light into a light reflected thereby and a light transmitting therethrough at a different rate of light quantity, and the fluoroscopic imaging element is arranged on the side where the larger light quantity comes out.

In the above X-ray radiograph apparatus, electric charges accumulated in the image area of the radiographic imaging element is cleared by a reset signal, and this reset signal is released in response to a start signal of X-ray irradiation.

Furthermore, the invention also provides an X-ray radiograph apparatus which comprises a bed for supporting a subject body lying thereon; an X-ray source for irradiating the subject body with X rays; an X-ray image intensifier for converting an X-ray image, which has transmitted through the subject body, into an optical image; a distributor which distributes the output optical image from the X-ray image intensifier to a plurality of optical paths and outputs the optical image in the direction parallel with the longitudinal direction of the bed; and an image pickup device consisting of imaging elements which are arranged on respective optical paths to receive the optical images output from the distributor.

In the above X-ray radiograph apparatus, one of imaging elements of the image pickup device is an imaging element for fluoroscopy while the other is an imaging element for radiography which has a higher resolution than the imaging element for fluoroscopy.

In the above X-ray radiograph apparatus, a plurality of optical paths receiving the output from the distributor are provided to direct the same direction.

In the above X-ray radiograph apparatus, the output optical paths from the distributor are arranged in a plane in parallel with the surface of the bed.

In the above X-ray radiograph apparatus, the output optical paths from the distributor are arranged in a plane intersecting the surface of the bed.

In the above X-ray radiograph apparatus, the output optical paths from the distributor are arranged to separate each other directing to the opposite directions.

DETAILED DESCRIPTION OF PREFERRED EMBODIMENTS

Figure 1:
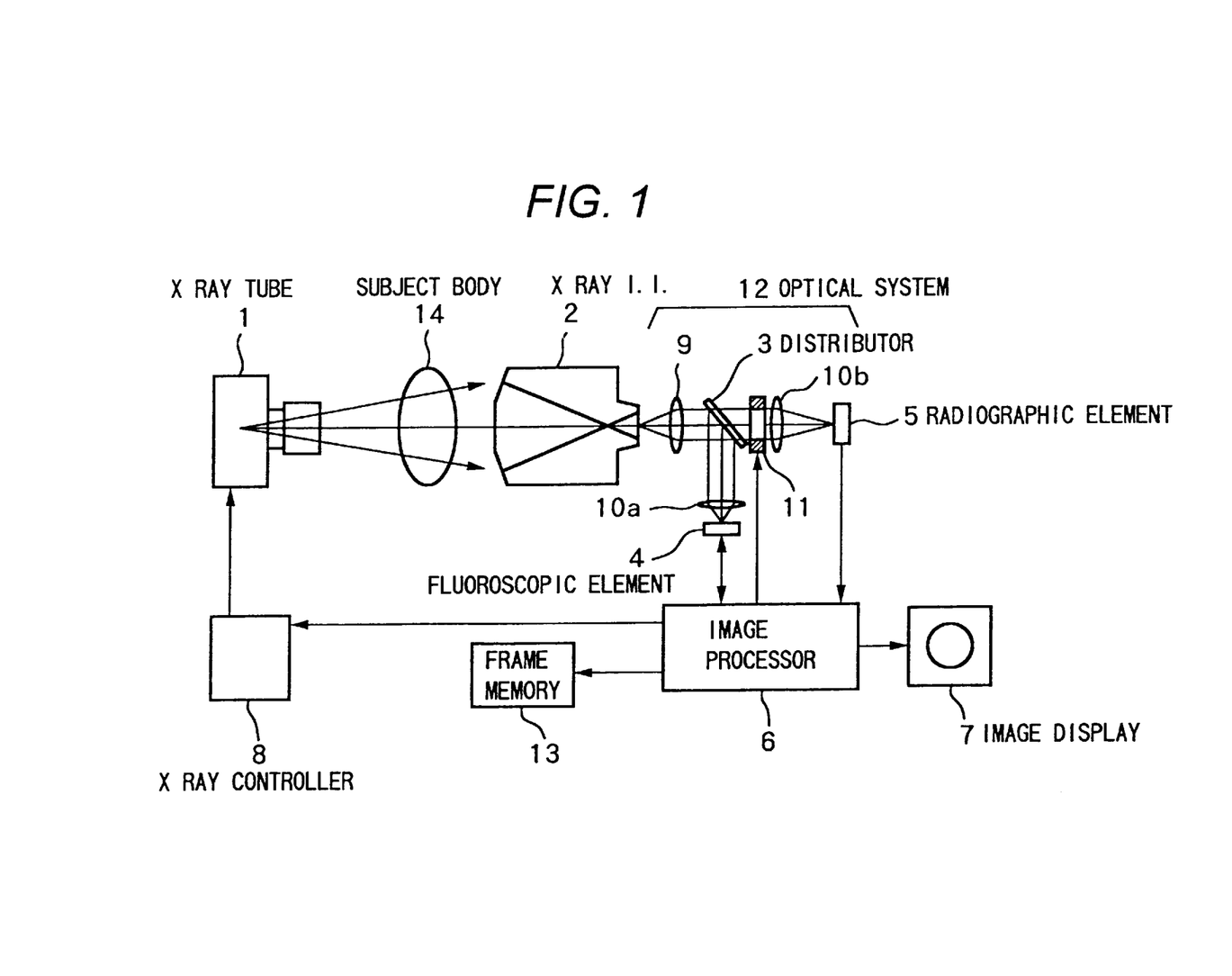
FIG. 1 is a block diagram showing an embodiment of an X-ray radiograph apparatus according to the invention.

FIG. 1 is a block diagram showing an ambodiment of an X-ray radiograph apparatus according to the invention. This X-ray radiograph apparatus irradiates a subject body with X rays to produce a fluoroscopic or radiographic image of a diagnostic part of the subject body with the help of some devices such as an X-ray image intensifier and a television camera, and displays an image on the screen of an image display. The apparatus includes, as shown in FIG. 1, an X-ray tube 1, an X-ray image intensifier 2 (referred to as X-ray I.I.2 hereinafter), a distributor 3, a plurality of imaging elements (4, 5), an image processor 6 and an image display 7

The X-ray tube 1 is used as an X-ray source for irradiating a subject body 14 with X rays and is arranged to receive an electric power from an X-ray controller 8 and to perform a predetermined X-ray irradiation against the subject body 14. An X-ray image which is produced by X rays coming from the X-ray tube 1 and then penetrates through the subject body 14, is converted into an optical image by the X-ray I.I. 2 which is constructed as combination of a plurality of photomultiplier tubes. The distributor 3 operates to distributively output the optical image output from the X-ray I.I. 2 to a plurality of optical paths at the same time, for instance it may be constructed of a half-mirror which distributively outputs an identical output optical image to a plurality of optical paths and which divides an incident light into a light reflected thereby and a light transmitting therethrough at a different rate of light quantity. The half-mirror is arranged to make an angle of about 45° with respect to the incident light, for instance.

Before and after the distributor 3 is provided an optical system 12 which includes a primary lens 9, secondary lenses 10a, 10b, and a shutter 11. The primary lens 9 converts the output light from the X-ray I.I. 2 into parallel right rays. One (10a) of the secondary lenses 10a, 10b converges the parallel light rays, of which the optical path is changed by the distributor 3, to a focal point while the other 10b converges the parallel light rays passing through the distributor 3 to another focal point. The shutter 11 acts to allow the parallel light rays passing through the distributor 3 to pass therethrough or not. A plurality of imaging elements (4, 5) convert the entirety of each optical image distributed by the distributor 3, into electrical signals (video signals) and are formed of charge-coupled devices (CCDs).

The image processor 6 takes in respective electrical signals from the imaging elements (4, 5) and performs the image processing thereof for displaying. For instance, a video processor may constitute the image processor 6. Furthermore, the image display 7 receives image signals from the image processor 6 and displays the image corresponding thereto. For instance, a television monitor may function as the image display 7. Furthermore, in FIG. 1, a reference numeral 13 designates a frame memory which receives the image signals from the image processor 6 and stores them therein.

In the invention, one of the above plural imaging elements (4, 5) is used as the fluoroscopic imaging element 4 for producing a fluoroscopic image while the other is used as the radiographic imaging element 5 for producing a radiographic image, and it is defined that the latter has a higher resolution than the former and has a slower imaging speed than the same. The fluoroscopic imaging element 4 fluoroscopes the subject body 14 with a low level radiation dose and contains pixels of one million, for instance CCD imaging element of 1000×1000 pixels. Its imaging speed is about 30 images per minute or so. On the other hand, the radiographic imaging element 5 radiographs the subject body 14 with a high level radiation dose and contains pixels of four millions, for instance CCD imaging elements of 2000×2000 pixels. The exposure time of the imaging element 5 is made variable and the shutter 11 arranged in front of the imaging element 5 is made to open in response to the start signal of X-ray irradiation in the radiographing operation, and is made to close in response to the finish signal indicative of completion of the exposure to the imaging element 5.

When the half-mirror used as the distributor 3 distributively outputs the identical output optical image from the X-ray I.I. 2 to a plurality of optical paths at the same time, it distributes the light quantity of the optical image at a different distribution ratio. For instance, the incident light of 8/10 is reflected by the half-mirror to be introduced to the fluoroscopic imaging element 4 while the remaining of 2/10 passes through the half-mirror to propagate toward the radiographic imaging element 5. The distribution ratio of the light quantity may be set, by taking account of such conditions as the exposure time per image in the fluoroscopic or radiographic mode operation, the quantum efficiency of the fluoroscopic imaging element 4 or the radiographic imaging element 5, the number of pixels of the fluoroscopic imaging element 4 or the radiographic imaging element 5, the sensitivity of the entire system including the optical system 12, etc., in such a manner that the electric charges accumulated per pixel frame of the fluoroscopic imaging element 4 on which incidence of the largest light quantity is supposed to occur, becomes the almost maximum accumulated electric charges of that pixel frame in the fluoroscopic operation, and also that the electric charges accumulated per pixel frame of the radiographic imaging element 5 on which incidence of the largest light quantity is supposed to occur, becomes the almost maximum accumulated electric charges in the radiographic operation. In this case, the X-ray condition in the radiographic mode operation is about 100 times as much as that in the fluoroscopic mode operation, so that even if the distribution ratio of the light quantity is made small as described above, the sufficient light quantity is secured for the radiographic imaging element 5.

The fluoroscopic imaging element 4 is preferably constituted by using such a CCD of the frame-transfer type or interline-type by which electronic shutter operation is made possible, thereby enabling adjustment of the imaging sensitivity to be carried out instantaneously after changing the exposure time. Also, the radiographic imaging element 5 is preferably constituted by using a CCD of the full-frame type suitable for the multi-pixel use. Furthermore, an optical diaphragm means (not shown) may be arranged in front of the fluoroscopic imaging element 4 in order to adjust the quantity of incident light thereof, thereby reducing the incident light quantity on the fluoroscopic imaging element 4 by means of the optical diaphragm means when radiographing the subject body by the radiographic imaging element 5. In this way, it becomes possible for the image radiographed by the radiographic imaging element 5 to be monitored by the fluoroscopic imaging element 4 at the same time.

The image processor 6 processes the X-ray fluoroscopic image signals taken by the fluoroscopic imaging element 4 and/or the radiographic image signals taken by the radiographic imaging element 5 to combine them for displaying on the image display 7. Furthermore, the image processor 6 processes the image signals of the pixels adjacent to a defect pixel in the radiographic imaging element 5 and the image signal of the pixel in the fluoroscopic imaging element 4 which corresponds to the defect pixel, to combine them for estimating the image signal of the above defect pixel.

The image display 7 displays a fluoroscopic image or a radiographic image produced based on respective output signals from the fluoroscopic imaging element 4 or the radiographic imaging element 5.

Next, the operation of the X-ray radiograph apparatus as constructed above will be described with reference to FIG. 2. In the fluoroscopic operation, X rays emitted from the X-ray tube 1 are irradiated and pass through the subject body 14 to form an X-ray image, which in turn is converted into an optical image through the X-ray I.I. 2. This optical image passes through the optical path including the primary lens 9, the distributor 3, and the secondary lens 10a, and then enters in the fluoroscopic imaging element 4 having a high frame rate such as 30 frames per second. At this time, the distributor 3 i.e. the half-mirror distributes 80% of the entire light quantity corresponding to the optical image to the fluoroscopic imaging element 4 as the incident light quantity thereto. The image signals of the image fluoroscoped by the fluoroscopic imaging element 4 is transmitted to the image display 7 through the image processor 6, thereby enabling the X-ray fluoroscopic image of the low level radiation dose to be observed through an image display screen. At this time, a reset signal is applied to the radiographic imaging element 5 of high resolution to clear the electric charges accumulated in its image area, thereby keeping the imaging element 5 in the waiting condition under which no accumulation of electric charge is allowed.

Figure 2A:
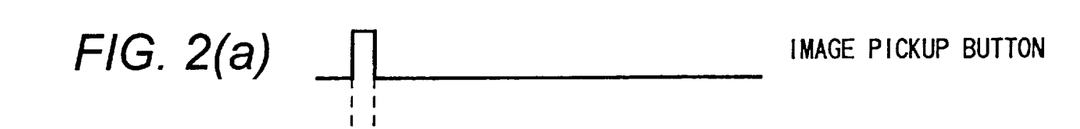
FIG. 2 is a timing diagram for explaining the operation of the X-ray radiograph apparatus.
Figure 2B:
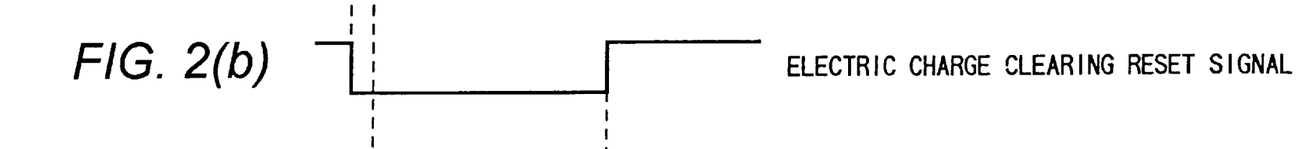
Figure 2C:
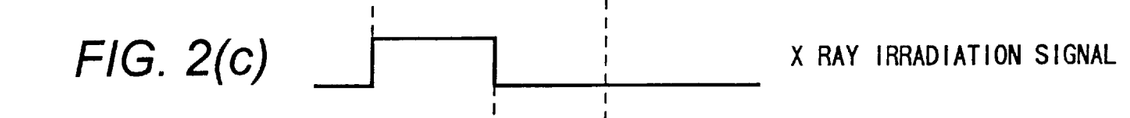

In the radiographic operation, as shown in FIG. 2(a), the operator monitors the X-ray fluoroscopic image on the screen of the image display 7 to timely presses a button. In synchronization with the start signal of X-ray irradiation by this button pressing, the radiographic imaging element 5 releases the reset signal for clearing the electric charge as shown in FIG. 2(b). After release of the reset signal, the X-ray irradiation signal is turned on as shown in FIG. 2(c), and X rays are emitted from the X-ray tube 1. The X-ray image resulting from penetration of X rays through the subject body 14 is converted into an optical image through the X-ray I.I. 2. This optical image enters in the radiographic imaging element 5 through the optical path including the primary lens 9, the distributor 3, shutter 11, and the secondary lens 10b. Then, the image signals taken by the radiographic imaging element 5 is transmitted to the image processor 6.

Figures 2D, 2E:
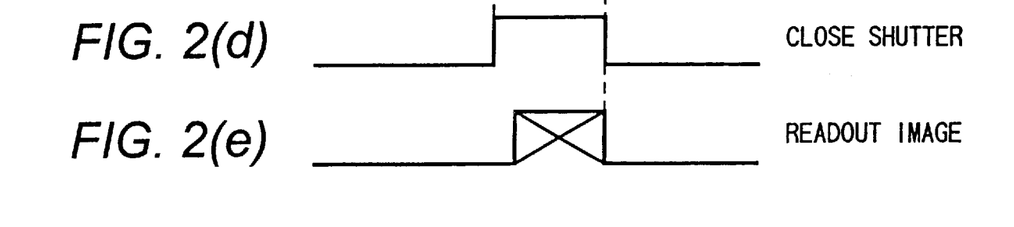

When the radiographing by X-ray irradiation is finished, the high speed shutter 11 such as a mechanical shutter, an electronic shutter, or a liquid crystal shutter, which is arranged in front of the radiographic imaging element 5 is immediately closed as shown in FIG. 2(d). With this, readout of the image can be started and the fluoroscopic operation by the fluoroscopic imaging element 4 can be reopened as shown in FIG. 2(e). When readout of the image is over, the reset signal for clearing electric charge is applied and the shutter 11 is opened to prepare for the next imaging step.

At the time of X-ray radiographing, a large quantity of light is introduced to the fluoroscopic imaging element 4. At this time, in order for the pixel, on which incidence of the largest light quantity occurs, to be not saturated with electric charges, the optical diaphragm means (not shown) arranged in front of the fluoroscopic imaging element 4 reduces the quantity of receiving light to extent that the incident light quantity on that pixel multiplied by the quantum efficiency becomes the maximum saturated electric charge.

Figure 3A:
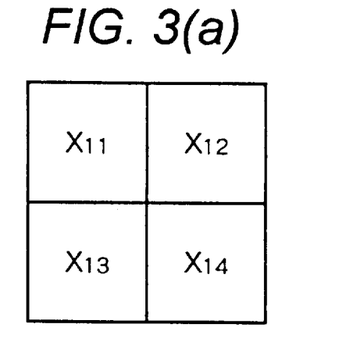
FIG. 3 is an illustration for explaining a processing for composing images.
Figure 3B:
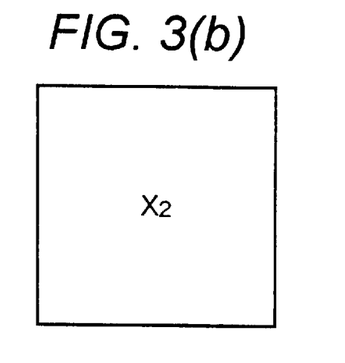

In the image processor 6, the image radiographed by the radiographic imaging element 5 is combined with the image (e.g. image of 1000×1000 pixels) fluoroscoped by the fluoroscopic imaging element 4 at the same time when the above radiographic image is produced, thereby enabling an image to be obtained at a high S/N ratio. This composition processing will be described with reference to FIG. 3. FIG. 3(a) shows certain four adjacent pixels $X_{11}$, $X_{12}$, $X_{13}$, $X_{14}$ in the image (e.g. 2000×2000 pixels) obtained by radiographic imaging element 5 and pixel values thereof. FIG. 3(b) illustrates a pixel $X_2$ and its pixel value in the fluoroscopic image (e.g. 1000×1000 pixels) obtained by the fluoroscopic imaging element 4, the pixel $X_2$ being one in a part indicative of the same position as shown in FIG. 3(a) with respect to the optical image output by the X-ray I.I. 2.

In the image of 2000×2000 pixels which is produced through composition processing in the image processor 6, let Xa be a new pixel value of part indicative of the pixel $X_{11}$, r be a constant for improving an S/N ratio, and k be a constant, Xa can be expressed as:

$$Xa = r(X_{11}+X_{12}+X_{13}+X_{14})/4 + (1-r)X_2 + \\ k(3X_{11}-X_{12}-X_{13}-X_{14})/4 \\ = [(3k+r)X_{11}-(k-r)(X_{12}+X_{13}+X_{14})]/4 + (1-r)X_2 \quad (1)$$

This means that the S/N ratio of the composed image is more improved by dividing the image signals radiographed by the radiographic imaging element 5 into a high spatial frequency component and a low spatial frequency component, and adding, these components to the image signals fluoroscoped by the fluoroscopic imaging element 4, with respectively weighted. At this time, an S/N ratio best for the image will be obtained if r:(1−r) is made to be almost equal to the square of a ratio between the S/N ratio of the low spatial frequency component of the image signals radiographed by the radiographic imaging element 5 and the S/N ratio of the image signals fluoroscoped by the fluoroscopic imaging element 4. This is because if r:(1−r)=$\alpha^2$:$\beta^2$ ($\alpha$, $\beta$: S/N of respective images), the S/N of the composed image is expressed as $\sqrt{(\alpha^2+\beta^2)}$. This means that the S/N becomes maximum. Furthermore, the edge will be emphasized by gradually increase the value of k from 1, if so desired. Contrary to this, if smoothing of it is preferable, it will be carried out by gradually decrease the value of k from 1.

On one hand, in case the pixel $X_{11}$ in the image of 2000×2000 pixels is defective, the pixel value at the corresponding position in the composed image is expressed as:

$$Xa=4X_2-X_{12}-X_{13}-X_{14} \quad (2)$$

At this time, the sensitivity of the radiographic imaging element 5 and the fluoroscopic imaging element 4 may be corrected based on the values of the pixels immediately in the vicinity of pixels $X_2$, and $X_{12}$, $X_{13}$, and $X_{14}$.

By the way, the distributor 3 as shown in FIG. 1 is constituted with a half-mirror. However, it should be noted that the invention is not limited to this example. Any other means may be used if it may distributively output the output optical images from the X-ray I.I. 2 through a plurality of optical paths. For instance, a rotary mirror may be used which rotates in one direction switching a light to a plurality of light paths.

Figure 4:
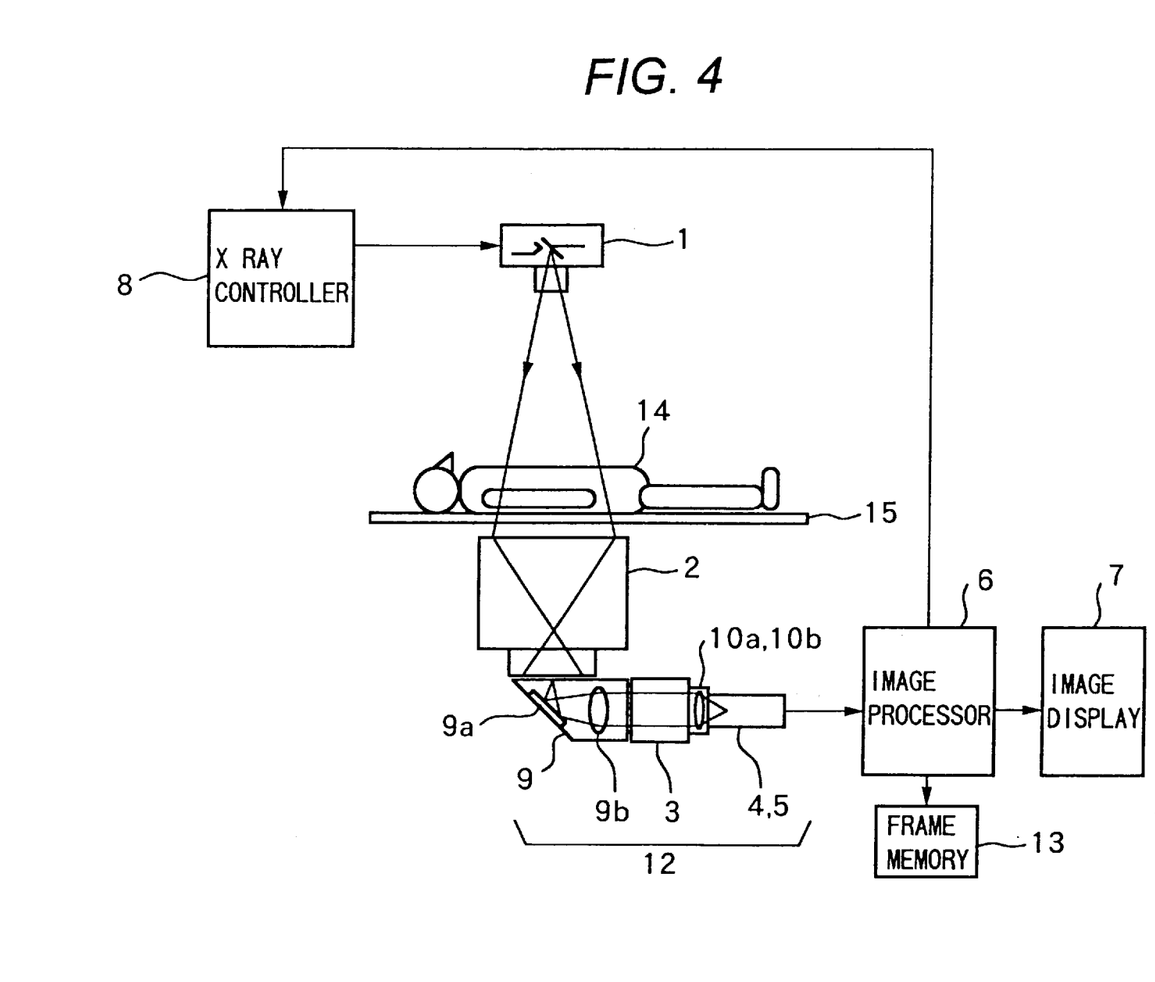
FIG. 4 is a schematic side view of another embodiment of X-ray radiograph apparatus according to the invention in case of viewing it from the side of a bed supporting a subject body lying thereon.

FIG. 4 is a schematic view of another embodiment of the X-ray radiograph apparatus according to the invention and is a side view showing the state where the subject body 14 is lying on a bed 15. This embodiment indicates the case that the invention is applied to an X-ray radiograph apparatus of the over-tube type in which an image pickup device such as the fluoroscopic imaging element 4 and the radiographic imaging element 5, is arranged under the bed 15. In the X-ray radiograph apparatus of the over-tube type like this, if the output optical image from the X-ray I.I. 2 is distributed to two directions perpendicular to each other by using the distributor 3 as shown in FIG. 1, and if the image pickup system such as the fluoroscopic imaging element 4 and the radiographic image element 5 is arranged under the bed 15 in such a way that one of the imaging elements is disposed lobgitudinally to the bed 15 and the other is set perpendicularly thereto, the entire scale of the image pickup system itself inevitably becomes large, which results in occupying a large space. However, in case that the image pickup system follows the arrangement as mentioned above, that is, one of the imaging element is directed perpendicularly to the longitudinal direction of the bed 15 or to the subject body axis, if it is needed for an operator (diagnostician) to access and stand near by the bed side from that direction, it might happen that his or her feet and/or legs unintentionally coming under the bed bump against the head of the imaging element moving toward him or her. Contrary to this, let us consider the case where the image pickup system is arranged in such a manner that one imaging element of it directs to the supporting legs of the bed 15 which stand opposing to the operator's standing position. In this case, the root portion of the bed supporting legs is projecting to the central portion of the bed 15, so that it might happen that the head of the imaging element collides with the bed supporting leg when the image pickup system moves in the direction perpendicular to the subject body axis. Thus, the smooth radiographing is disturbed and the image pickup system might be damaged.

The embodiment of the invention as shown in FIG. 4 is for overcoming the difficulties as mentioned above. In this embodiment, the distributor 3 is constituted in such a manner that it distributes the identical output optical image to a plurality of paths and outputs each of distributed optical images within a range of the width of the bed 15 supporting the subject body 14 lying thereon and in the direction almost in parallel to the longitudinal direction of the bed 15. In FIG. 4, the X-ray tube 1 is arranged above the bed 15 supporting the subject body 14 lying thereon. The X-ray I.I. 2 is arranged under the bed 15 to be located in a position opposing to the X-ray tube 1. The optical system 12 is located on the bottom side of the X-ray I.I. 2 so as to face to the optical image output face thereof, and is provided with the primary lens 9 and the secondary lenses 10a, 10b. The primary lens 9 includes a total reflection mirror 9a and a lens body 9b. This lens 9 acts to bend the optical path of the output optical image from the X-ray I.I. 2 in the lateral direction with respect to the X-axis by an angle of 90° and converts the optical image into that which is formed of parallel light rays, thus enabling the dimension of the image pickup system in the X-axis direction to be shortened.

The distributor 3 is located on the optical path of the output optical image from the lens 9. As described above, this distributor 3 distributes the identical output optical image to a plurality of optical paths and outputs each of distributed optical images within a range of the width of the bed 15 supporting the subject body 14 lying thereon and in the direction almost in parallel to the longitudinal direction of the bed 15, and is constituted in the way as shown in FIG. 5. This figure is a diagrammatic bottom view of an assembly including the primary lens 9, the distributor 3, the fluoroscopic imaging element 4 and the radiographic imaging element 5.

Figure 5A:
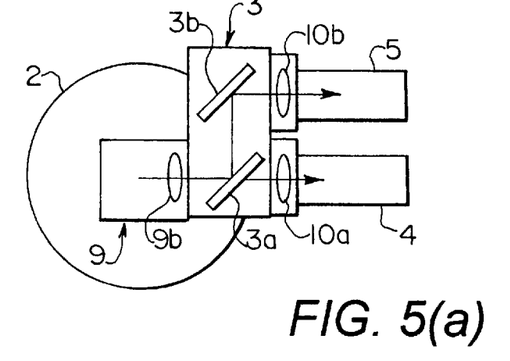
FIG. 5 is a bottom view of an assembly of primary lens, distributor, fluoroscopic imaging element, and radiographic imaging element.

As shown in FIG. 5(a), the distributor 3 includes a half-mirror 3a which is located on the optical path of the output optical image from the primary lens 9 making an angle of 45° with respect to the optical path, and a total reflection mirror 3b which is arranged to stand side by side in parallel with the half-mirror 3a within a range of the width of the bed 15 also making an angle of 45° with respect to the optical path. When the half-mirror 3a distributes simultaneouly the output optical image from the primary lens 9 to a plurality of optical paths by allowing the incident light of 8/10 to pass therethrough and reflecting the remaining 2/10, it distributes the light quantity at different distribution rates. The total reflection mirror 3b once receives the light reflected by the half-mirror 3 and reflects it entirely. As the half-mirror 3a and the total reflection mirror 3b are arranged in parallel so as to commonly make an angle of 45° with respect to the optical path of the output optical image from the primary lens 9, the light passing through the half-mirror 3a is made to be parallel to the light which is once reflected by the half-mirror 3a and again totally reflected by the total reflection mirror 3b and respective optical paths direct in the same direction. As shown in FIG. 4, the light distributed by the half-mirror 3a and the total reflection mirror 3b is made to be almost parallel to the longitudinal direction of the bed 15 supporting the subject body 14 lying thereon.

As shown in FIG. 5(a), on the optical path of the light passing through the half-mirror 3a are arranged the secondary lens 10a and the fluoroscopic imaging element 4. This secondary lens 10a serves to focus the parallel light rays passing through the half-mirror 3a on the image pickup surface of the fluoroscopic imaging element 4. On the optical path of the reflected light from the total reflection mirror 3b are arranged the secondary lens 10b and the radiographic imaging element 5. This secondary lens 10b serves to focus the parallel light rays reflected by the total reflection mirror 3b on the image pickup surface of the radiographic imaging element 5. As will be readily seen from FIGS. 4 and 5(a), these fluoroscopic imaging element 4 and radiographic imaging element 5 are positioned in parallel with each other and arranged within a range of the width of the bed 15 supporting the subject body 14 lying thereon and almost in parallel to the longitudinal direction of the bed 15.

Consequently, in the embodiment as shown in FIG. 4, the image pickup system such as the fluoroscopic imaging element 4 and the radiographic imaging element 5 is arranged under the bed 15 to be positioned within a range of the width of the bed 15, so that the entire scale of the image pickup system is made compact, thus enabling the space occupied thereby to be smaller. As a result of this, the image pickup system can prevent its head portion from bumping against the feet and/or legs of the operator or the supporting legs of the bed 15 while it moves back and forth. Thus, it becomes possible for fluoroscoping and/or radiographing to be smoothly carried out without giving any accidental damage to the image pickup system.

Figure 5B:
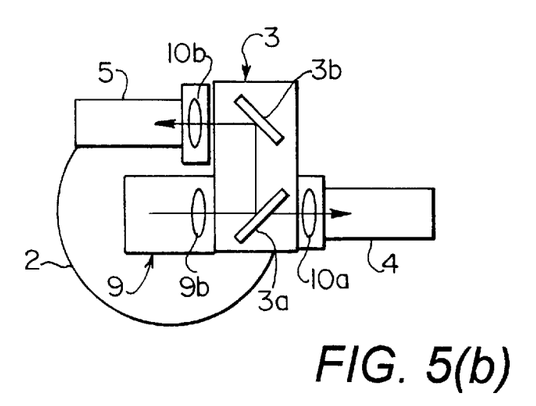

FIG. 5(b) is a bottom view of another distributor 3 which is modified based on that which is shown in FIG. 5(a). This modification results from such arrangement that the total reflection mirror 3b and the half-mirror 3a stand side by side so as to have their respective extension lines intersected each other at 90°. In this case, the optical path of the output optical image from the primary lens 9 to the fluoroscopic imaging element 4 remains as it is while the optical path of the output optical image from the primary lens 9 to the radiographic imaging element 5 is bent 180° by the total reflection mirror 3b and directs to the direction opposite to the optical path leading to the fluoroscopic imaging element 4. Namely, output optical paths from the half-mirror 3a and the total reflection mirror 3b are disposed to be separated each other directing to opposite directions. In this modified case, the fluoroscopic imaging element 4 and the radiographic imaging element 5 may be arranged in parallel with each other and also be arranged within a range of the width of the bed 15 supporting the subject body 14 lying thereon and almost in parallel with the longitudinal direction of the bed 15.

Figure 6:
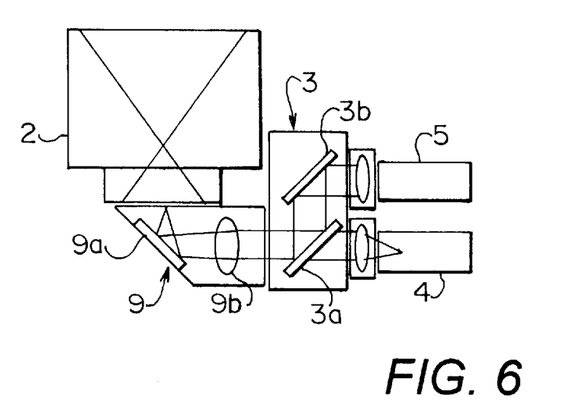
FIG. 6 is a side view of another distributor modified from that which is shown in FIG. 5.

FIG. 6 is a side view of another distributor 3 which is modified from that which is shown in FIG. 5. In the embodiments as shown in FIGS. 4 and 5(a), the half-mirror 3a and the total reflection mirror 3b which are constituting the distributor 3, are positioned side by side in a plane parallel to the surface of the bed 15. Contrary to this, in this modification as shown in FIG. 6, the half-mirror 3a and the total reflection mirror 3b are vertically disposed in a plane perpendicular to the surface of the bed 15. In this case, as will be apparently seen from FIG. 6, the output optical paths from the half-mirror 3a and the total reflection mirror 3b are arranged in a plane vertically intersecting the surface of the bed and the fluoroscopic imaging element 4 and the radiographic imaging element 5 are in parallel with each other taking upper and lower positions respectively, and are also positioned within a range of the width of the bed 15 supporting the subject body 14 lying thereon and in the direction almost in parallel to the longitudinal direction of the bed 15.

In the embodiments as shown in FIGS. 5 and 6, the distributor 3 is constituted with the half-mirror 3a and the total reflection mirror 3b. However, the half mirror 3a may be replaced by a total reflection mirror capable of rotating within an angular range of 45°. In this case, when turning the total reflection mirror (3a) by angle of 45° to make it be parallel to the optical path leading to the fluoroscopic imaging element 4, the output optical image from the primary lens 9 can be introduced to the fluoroscopic imaging element 4. Contrary to this, when turning the total reflection mirror (3a) by an angle of 45° in the opposite direction to make it intersect the optical path directing to the fluoroscopic imaging element 4 at an angle of 45°, the output optical image from the primary lens 9 can be led to the radiographic imaging element 5. Accordingly, the output optical image directed to the fluoroscopic imaging element 4 and the same directed to the radiographic imaging element 5 may be switched by the turning motion of the total reflection mirror (3a).

In the embodiments as shown in FIGS. 5 and 6, the lens body 9b of the primary lens 9 and the secondary lenses 10a, 10b constitute tandem lenses, respectively, and the optical path length between the lens body 9b and the secondary lens 10b becomes longer comparing with that between the lens body 9b and the secondary lens 10a. When the optical path length between tandem lenses is made longer, it might happen that the optical image transmitted through such comes to have a decreased peripheral light quantity.

Thus, let us describe the countermeasure against this in the following. In case the focal length and brightness of the primary lens and the secondary lens are fixed, it is possible to simply calculate the limit value of the tandem interval which causes no decrease in the peripheral light quantity (at this time, it is assumed that the aperture efficiency of respective lenses is 100°). Here, the situation is that light rays between lenses disposed in the tandem fashion are parallel light rays, a luminous flux coming from other than the optical axis is a parallel luminous flux inclining to the optical axis between two lenses, and a necessary lens diameter is determined with the height at which the main light rays intersect the lens surface. Under the situation like this, the tandem interval L is expressed as follows.

$$L=(f_1^2 F_2 - F_1 f_1 f_2)/(2 F_1 F_2 h_1) \quad (3)$$

where f$_1$: focal distance of lens body 9b of primary lens 9
f$_2$: focal distance of secondary lens 10b
F$_1$: F value of lens body 9b
F$_2$: F value of secondary lens 10b
h$_1$: radius of output surface of X-ray I.I. 2

It will be understood from the above expression (3) that the larger the F value (F$_2$) of the secondary lens 10b becomes, the larger the limit value of the tandem interval L becomes. Accordingly, when the half-mirror 3a and the total reflection mirror 3b as shown in FIGS. 5 and 6 are arranged within the range of tandem interval L less than the value attained by the expression (3), the image can be obtained without decrease in its peripheral light quantity.

What is claimed is:

1. An X-ray radiograph apparatus, comprising:
   a) an X-ray source that irradiates a subject body with X-rays of a low level radiation dose during a fluoroscopic operation, and that irradiates the subject body with X-rays of a high level radiation dose during a radiographic operation;
   b) an X-ray image intensifier for converting an X-ray image, formed when X-rays emitted from the X-ray source penetrate through the subject body, into an optical image;
   c) a distributor for distributing the optical image that is output from the X-ray image intensifier onto plural optical paths;
   d) a fluoroscopic imaging device, arranged on a first optical path from the distributor, for imaging an optical image output from the X-ray image intensifier during the fluoroscopic operation, the fluoroscopic imaging device having a first resolution and a first imaging speed;
   e) a radiographic imaging device, arranged on a second optical path from the distributor, for imaging an output optical image from the X-ray image intensifier during the radiographic operation, the radiographic imaging device having a second resolution that is higher than the first resolution and a second imaging speed that is lower than the first imaging speed; and
   f) an image display for displaying a fluoroscopic image or a radiographic image formed from respective output signals from the fluoroscopic imaging device and the radiographic imaging device.

2. The apparatus of claim 1, wherein:
   both the fluoroscopic imaging device and the radiographic imaging device include a charge-coupled device (CCD) imaging element.

3. The apparatus of claim 1, further comprising:
   an image processor that performs an image processing for displaying, on a screen of the image display, X-ray fluoroscopic image signals obtained from the fluoroscopic imaging device and/or X-ray radiographic image signals obtained from the radiographic imaging device.

4. The apparatus of claim 1, wherein:
   an output optical image from the distributor is input to both the fluoroscopic imaging device and the radiographic imaging device at the same time.

5. The apparatus of claim 3, wherein:
   the image processor produces image data for display with an improved signal-to-noise ratio by composing the X-ray fluoroscopic image signals and the X-ray radiographic image signals that are simultaneously output from the distributor.

6. The apparatus of claim 5, wherein:
   when a defective picture element occurs in an image signal due to a defect in a first one of the fluoroscopic imaging device and the radiographic imaging device, the image processor produces data for the defective picture element using a second one of the fluoroscopic imaging device and the radiographic imaging device.

7. The apparatus of claim 1, further comprising:
   a shutter located between the distributor and the radiographic imaging device.

8. The apparatus of claim 7, wherein:
   the shutter is opened in response to a start signal of X-ray irradiation for radiographing; and
   the shutter is closed in response to a signal indicative of an end of the radiographing.

9. The apparatus of claim 1, wherein:
   the distributor includes a half-mirror that divides incident light into reflected light and transmitted light that are different in quantity from each other; and
   the fluoroscopic imaging device is arranged on a side of the half-mirror from which comes a larger quantity of light.

10. The apparatus of claim 2, wherein:
    electric charges that accumulate in an image area of the CCD imaging element for radiographing are cleared by a reset signal that is released in response to a start signal of X-ray irradiation.

11. An X-ray radiograph apparatus, comprising:
    a) a bed for supporting a subject body;
    b) an X-ray source for irradiating the subject body with X-rays;
    c) an X-ray image intensifier for converting an X-ray image, formed when X-rays are transmitted through the subject body, into an optical image;
    d) a distributor that distributes the optical image from the X-ray image intensifier to plural mutually-separate optical paths, and that outputs the optical image in a direction along a longitudinal direction of the bed; and
    e) plural CCD imaging elements arranged on respective ones of the optical paths to receive the optical images output from the distributor, wherein:
       e1) a first one of the plural CCD imaging elements is a fluoroscopy CCD imaging element having a first resolution and a first imaging speed; and
       e2) a second one of the plural CCD imaging elements is a radiography CCD imaging element that has a second resolution that is higher than the first resolution, and a second imaging speed that is lower than the first imaging speed.

12. The apparatus of claim 11, wherein:
    the distributor includes a half-mirror that divides incident light into reflected light and transmitted light that are different in quantity from each other; and
    the fluoroscopy CCD imaging element is arranged on a side of the half-mirror from which comes a larger quantity of light.

13. The apparatus of claim 11, wherein:
    centers of the plural output paths from the distributor are arranged in a plane, and are separated from each other by at least one half-mirror and one total-reflection mirror.

14. The apparatus of claim 13, wherein:

the plural optical paths from the distributor are arranged in a plane parallel to a surface of the bed; and output directions of the optical paths are directed in a same direction.

15. The apparatus of claim 13, wherein:

the plural optical paths from the distributor are arranged in a plane that intersects a surface of the bed.

16. The apparatus of claim 13, wherein:

the plural optical paths from the distributor are arranged separate from each other and in opposite directions.

17. An X-ray radiograph apparatus, comprising:

a) a bed for supporting a subject body;

b) an X-ray source for irradiating the subject body with X-rays;

c) an X-ray image intensifier for converting an X-ray image, formed when X-rays are transmitted through the subject body, into an optical image;

d) a distributor that distributes the optical image from the X-ray image intensifier to plural mutually-separate optical paths, and that outputs the optical image in a direction along a longitudinal direction of the bed, wherein the distributor includes a half-mirror that divides incident light into reflected light and transmitted light that are different in quantity from each other; and e) plural CCD imaging elements, arranged on respective ones of the optical paths to receive the optical images output from the distributor, and including a fluoroscopy CCD imaging element that is arranged on a side of the half-mirror from which comes a larger quantity of light.

18. The apparatus of claim 17, wherein:

a first one of the plural CCD imaging elements is the fluoroscopy CCD imaging element that has a first resolution and a first imaging speed; and a second one of the plural CCD imaging elements is a radiography CCD imaging element that has a second resolution that is higher than the first higher resolution, and a second imaging speed that is lower than the first imaging speed.

19. The apparatus of claim 17, wherein:

centers of the plural output paths from the distributor are arranged in a plane, and are separated from each other by at least one half-mirror and one total-reflection mirror.

20. The apparatus of claim 19, wherein:

the plural optical paths from the distributor are arranged in a plane parallel to a surface of the bed; and output directions of the optical paths are directed in a same direction.

21. The apparatus of claim 19, wherein:

the plural optical paths from the distributor are arranged in a plane that intersects a surface of the bed.

22. The apparatus of claim 19, wherein:

the plural optical paths from the distributor are arranged separate from each other and in opposite directions.

* * * * *